US00PP12835P2

(12) United States Plant Patent
Lamb et al.

(10) Patent No.: US PP12,835 P2
(45) Date of Patent: Aug. 6, 2002

(54) SPATHIPHYLLUM PLANT NAMED 'DOUBLE TAKE'

(75) Inventors: Ann Elizabeth Lamb, Sebring; David R. Lilly, Boynton Beach, both of FL (US)

(73) Assignee: Twyford International, Inc., Santa Paula, CA (US)

( * ) Notice: Subject to any disclaimer, the term of this patent is extended or adjusted under 35 U.S.C. 154(b) by 0 days.

(21) Appl. No.: 09/828,117

(22) Filed: Apr. 6, 2001

(51) Int. Cl.[7] ..... A01H 5/00

(52) U.S. Cl. ..... Plt./364

(58) Field of Search ..... Plt./364

*Primary Examiner*—Bruce R. Campell
*Assistant Examiner*—Annette H. Para
(74) *Attorney, Agent, or Firm*—C. A. Whealy

(57) ABSTRACT

A distinct cultivar of Spathiphyllum plant named 'Double Take', characterized by its upright, outwardly arching and symmetrical plant habit; glossy dark green leaves; rapid growth rate; early, continuous and freely flowering habit; fragrant inflorescences; pure white spathes that are positioned well above the foliage on strong and erect peduncles; long-lasting spathes; and relative tolerance to low and high temperatures.

2 Drawing Sheets

BACKGROUND OF THE INVENTION

The present Invention relates to a new and distinct cultivar of Spathiphyllum plant, botanically known as Spathiphyllum hybrid, and hereinafter referred to by the cultivar name Double Take.

The new cultivar is a product of a planned and controlled breeding program conducted by the Inventors in Apopka, Fla. The objective of the breeding program is to create freely-flowering Spathiphyllum cultivars. The new cultivar originated from a deliberate cross made by the Inventors on Nov. 28, 1997 of the Spathiphyllum cultivar Jungfrau, disclosed in U.S. Plant Pat. No. 10,627, as the female or seed parent and the Spathiphyllum cultivar Sweet Pablo, disclosed in U.S. Plant Pat. No. 10,817, as the male or pollen parent. The cultivar Double Take was discovered and selected by the Inventors as a plant within the progeny of the stated cross in a controlled environment in Homestead, Fla., on Feb. 3, 1999.

Asexual propagation of the new cultivar by tissue culture since February, 1999, in a laboratory in Sebring, Fla., has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature, light intensity, fertilizer level and propagation procedures, without, however, any variance in genotype.

The following traits have been repeatedly observed and are determined to be the unique characteristics of 'Double Take'. These characteristics in combination distinguish 'Double Take' as a new and distinct cultivar:

1. Upright, outwardly arching and symmetrical plant habit.
2. Glossy dark green leaves.
3. Rapid growth rate.
4. Early, continuous and freely flowering habit.

5. Fragrant inflorescences.
6. Pure white spathes that are positioned well above the foliage on strong and erect peduncles.
7. Long-lasting spathes.
8. Relative tolerance to low and high temperatures.

Plants of the new Spathiphyllum differ from plants of the female parent, the cultivar Jungfrau, when grown in side-by-side comparisons in Sebring, Fla., in the following characteristics:

1. Plants of the new Spathiphyllum are more upright than plants of the cultivar Jungfrau.
2. Plants of the new Spathiphyllum have larger and glossier leaves than plants of the cultivar Jungfrau.
3. Plants of the new Spathiphyllum are less susceptible to chilling injury and heat stress than plants of the cultivar Jungfrau.

Plants of the new Spathiphyllum differ from plants of the male parent, the cultivar Sweet Pablo, when grown side-by-side comparisons in Sebring, Fla., in the following characteristics:

1. Plants of the new Spathiphyllum are more compact than plants of the cultivar Sweet Pablo.
2. Plants of the new Spathiphyllum are more freely and continuous flowering than plants of the cultivar Sweet Pablo.

Plants of the new Spathiphyllum can be compared to plants of the cultivar Petite, not patented. However, in side-by-side comparisons conducted by the Inventors in Sebring, Fla., plants of the new Spathiphyllum differ from plants of the cultivar Petite in the following characteristics:

1. Plants of the new Spathiphyllum are more outwardly spreading and not as upright as plants of the cultivar Petite.
2. Plants of the new Spathiphyllum grow more rapidly than plants of the cultivar Petite.
3. Plants of the new Spathiphyllum have larger, wider, longer and more rugose leaves than plants of the cultivar Petite.
4. Plants of the new Spathiphyllum are less susceptible to chilling injury than plants of the cultivar Petite.

5. Plants of the new Spathiphyllum are more freely and continuous flowering than plants of the cultivar Petite.

BRIEF DESCRIPTION OF THE PHOTOGRAPHS

The accompanying colored photographs illustrate the overall apparance of the new cultivar, showing the colors as true as it is reasonably possible to obtain in colored reproductions of this type. Colors in the photographs may differ slightly from the color values cited in the detailed botanical description which accurately describe the colors of the new Spathiphyllum.

The photograph on the first sheet comprises a side perspective view of a typical 7-month old plant of 'Double Take' grown in a 15-cm container.

The photograph on the second sheet comprises a close-view of a typical inflorescence and leaves of a plant of 'Double Take' grown for 7 months in a 15-cm container.

DETAILED BOTANICAL DESCRIPTION

The following observations, measurements and comparisons describe 7-month old plants (from planting rooted tissue-cultured plantlets) grown in Apopka, Fla., in a polyethylene-covered greenhouse and under commercial production conditions in 15-cm containers. During the production of the plants, day temperatures ranged from 70 to 90° F., night temperatures ranged from 65 to 75° F., and light levels were about 1,500 foot-candles.

In the following description, color references are made to The Royal Horticultural Society Colour Chart except where general terms of ordinary dictionary significance are used.

Botanical classification: Spathiphyllum hybrid cultivar Double Take.

Parentage:

*Female parent*.—Spathiphyllum hybrid cultivar Jungfrau, disclosed in U.S. Plant Pat. No. 10,627.

*Male parent*.—Spathiphyllum hybrid cultivar Sweet Pablo, disclosed in U.S. Plant Pat. No. 10,817.

Propagation:

*Type*.—By tissue culture.

*Time to initiate roots on a tissue-cultured cutting*.—Summer: About 6 to 8 days at 70 to 90° F., day temperature, and 65 to 75° F., night temperature. Winter: About 7 to 10 days at 70 to 90° F., day temperature, and 65 to 75° F., night temperature.

*Time to produce a fully-rooted tissue-cultured plantlet*.—Summer: About 70 days at 70 to 90° F., day temperature, and 65 to 75° F., night temperature. Winter: About 84 days at 70 to 90° F., day temperature, and 65 to 75° F., night temperature.

*Root description*.—Thick, white, fleshy; lateral branch roots, fine.

*Rooting habit*.—Freely branching.

Plant description:

*Plant shape*.—Upright, outwardly arching and symmetrical plant habit; intermediate in stature.

*Growth habit*.—Erect when young, becoming outwardly arching as leaves develop. Freely clumping and full appearance. Plants of the new Spathiphyllum are typically grown in 10 to 15-cm containers, but can also be grown in 20-cm or larger-sized containers.

*Plant height*.—About 38 cm from soil level to top of leaf plane.

*Plant spread*.—About 52 cm.

*Growth rate*.—Rapid growth rate; about 6 to 7 months are required to produce a finished flowering plant in 15-cm container from a rooted tissue-cultured plantlet.

*Foliage description*.—Length: About 28.5 cm. Width: About 11.75 cm. Shape: Narrowly ovate. Apex: Elongated acuminate. Base: Obtuse. Margin: Entire, somewhat undulate. Aspect: Initially upright, then somewhat reflexed towards apex. Surface: Rugose; midrib and lateral veins, sunken on upper surface and prominent on lower surface. Texture, both surfaces: Leathery, smooth, glabrous, durable and flexible. Color: Young, upper surface: Close to 147A, glossy. Young, lower surface: More green than 147B. Mature, upper surface: Darker than 147A, glossy. Mature, lower surface: More green than 147B. Petiole: Aspect: Initially erect, outer leaves about 40 to 45° from vertical with development; slight outward bend at base of geniculum. Length: About 20.5 cm. Diameter, base: About 8 mm. Diameter, just below geniculum: About 4 mm. Wing length: About 16.5 cm. Wing width: About 6 mm. Geniculum length: About 2.8 cm. Geniculum diameter: About 5 mm. Strength: Strong, but flexible. Color: Closest to 146A.

Inflorescence description:

*Inflorescence arrangement/quantity* .—Concave spathes with spadices held well above the foliage on strong and erect peduncles. Freely flowering; typically about 5 developing and open spathes per plant at one time; inflorescences arise from leaf axils.

*Time to flower*.—Plants flower very early, often before planting rooted plantlets into the final containers. Plants of the new Spathiphyllum flower continuously and flower year-round under greenhouse production conditions.

*Inflorescence longevity*.—Spathes generally maintain white color for about 4 to 6 weeks on the plant. As cut flowers, spathes maintain good substance for about 7 days.

*Fragrance*.—Moderately fragrant, sweet, typical of Spathiphyllum.

*Spathe*.—Length: About 14.5 cm. Width: About 8 cm. Shape: Ovate. Apex: Elongated acuminate. Base: Obtuse. Aspect: Concave, curling over the spadix. Color, both surfaces: White, closest to 155D, becoming green, close to 144A, with development. Back surface midvein, 146A.

*Spadix*.—Length: About 6.8 cm. Diameter: About 1.4 cm. Color: 158C to 158D becoming green, closest to 143A, with development. Quantity of flowers: More than 200 per spadix. Pollen: Abundant, white, close to 155D.

*Peduncle*.—Aspect: Very strong. Length: Base of peduncle to base of spathe: About 42 cm. Base of spathe to stipe: About 2.5 cm. Stipe: About 7.5 mm. Diameter, at base of spathe: About 5 mm. Diameter, at base of peduncle: About 7 mm. Color: Close to 146A.

*Seed*.—Seed development has not been observed.

Disease/pest resistance: Plants of the new Spathiphyllum have not been observed to be resistant to pathogens or pests common to Spathiphyllum.

Temperature tolerance: Plants of the new Spathiphyllum have heen shown to be relatively resistant to chilling injury and tolerate temperatures as low as 38° F. with only slight foliar injury. Plants of the new Spathiphyllum have been shown to be relatively tolerant to heat stress and tolerate temperatures as high as 104° F. with only slight foliar injury.

It is claimed:

1. A new and distinct cultivar of Spathiphyllum plant named 'Double Take', as illustrated and described.

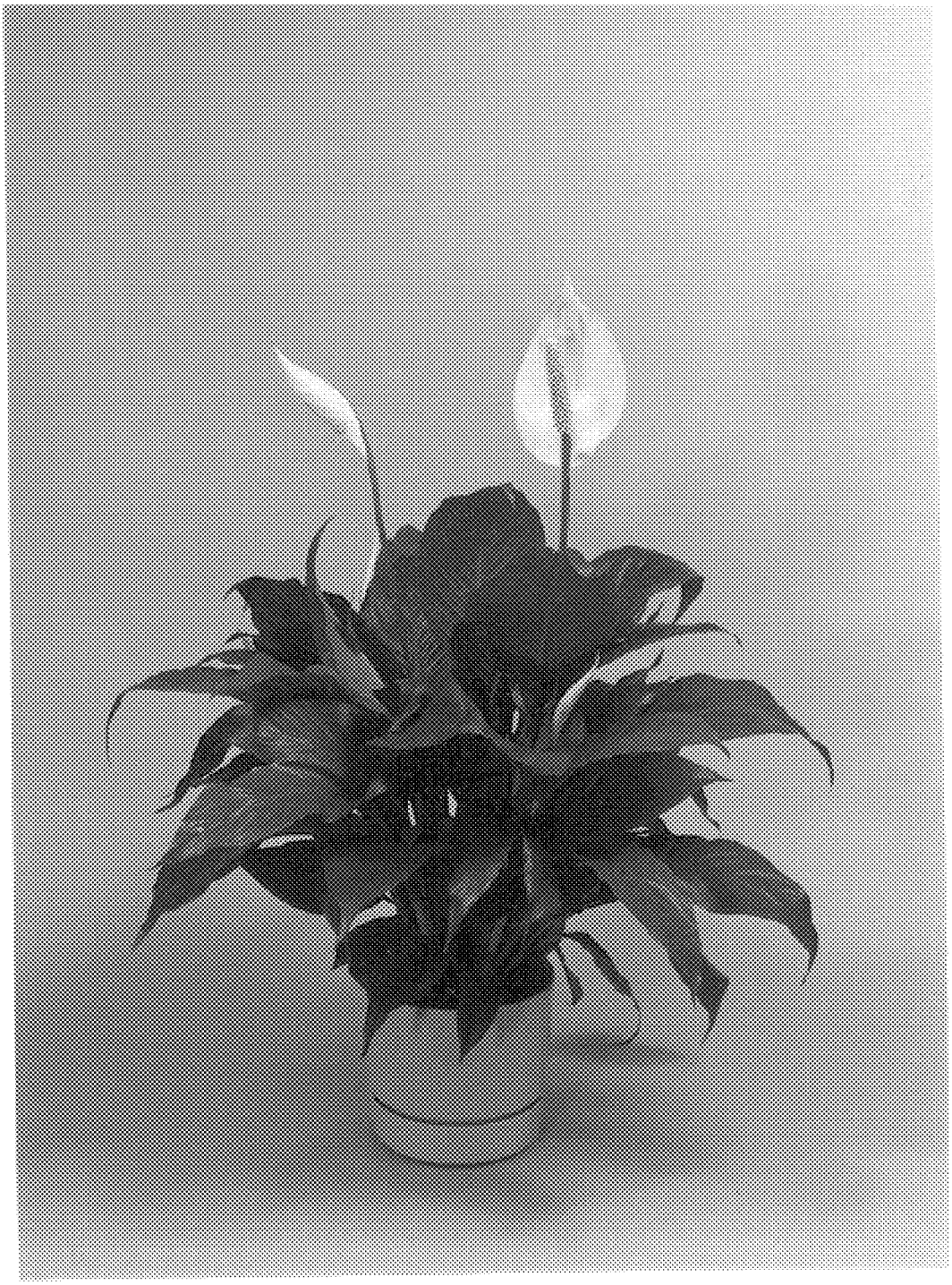

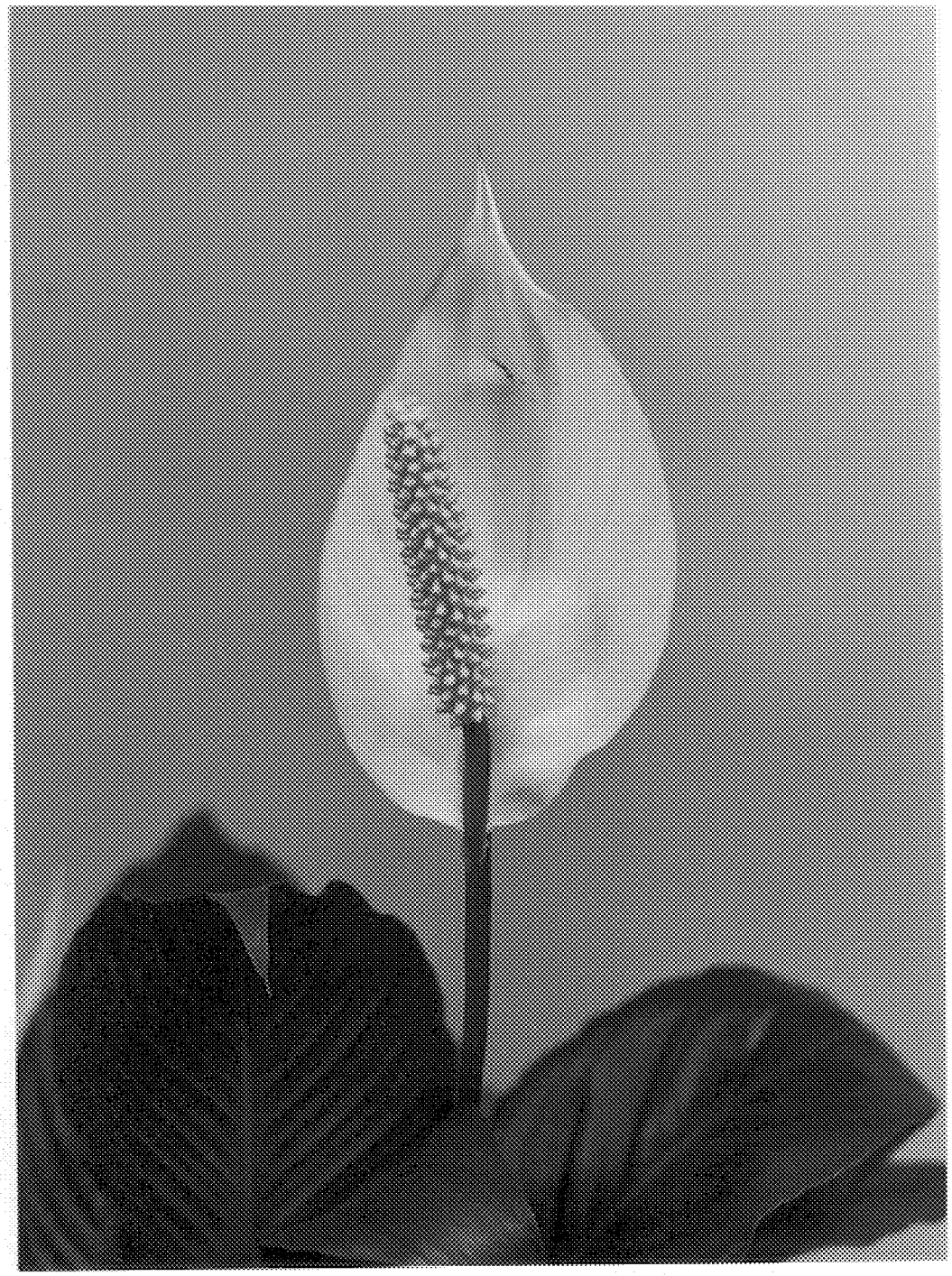

* * * * *